(12) United States Patent
Stevenson et al.

(10) Patent No.: US 10,835,216 B2
(45) Date of Patent: Nov. 17, 2020

(54) SPINNERET FOR MANUFACTURE OF MELT BLOWN NONWOVEN FABRIC

(71) Applicant: Covidien LP, Mansfield, MA (US)

(72) Inventors: Richard Stevenson, Colchester, CT (US); Seth Gleiman, Branford, CT (US)

(73) Assignee: COVIDIEN LP, Mansfield, MA (US)

( * ) Notice: Subject to any disclaimer, the term of this patent is extended or adjusted under 35 U.S.C. 154(b) by 921 days.

(21) Appl. No.: 14/582,257

(22) Filed: Dec. 24, 2014

(65) Prior Publication Data

US 2016/0183929 A1 Jun. 30, 2016

(51) Int. Cl.
| | |
|---|---|
| *A61B 17/00* | (2006.01) |
| *A61B 17/072* | (2006.01) |
| *D01D 4/02* | (2006.01) |
| *D01D 5/098* | (2006.01) |
| *D01D 5/08* | (2006.01) |

(52) U.S. Cl.
CPC ........ *A61B 17/00* (2013.01); *A61B 17/07292* (2013.01); *D01D 4/02* (2013.01); *D01D 4/025* (2013.01); *D01D 5/082* (2013.01); *D01D 5/0985* (2013.01); *A61B 2017/00526* (2013.01); *D10B 2401/12* (2013.01); *D10B 2509/00* (2013.01)

(58) Field of Classification Search
CPC .......... D01D 4/02; D01D 4/025; D01D 5/082; D01D 5/0985
See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov et al. |
| 3,124,136 A | 3/1964 | Usher |
| 3,364,200 A | 1/1968 | Ashton et al. |
| 3,490,675 A | 1/1970 | Green et al. |
| 3,499,591 A | 3/1970 | Green |
| 3,939,068 A | 2/1976 | Wendt et al. |

(Continued)

FOREIGN PATENT DOCUMENTS

| | | |
|---|---|---|
| CA | 2 667 434 A1 | 5/2008 |
| DE | 19924311 A1 | 11/2000 |

(Continued)

OTHER PUBLICATIONS

Extended European Search Report corresponding to EP 13 19 4995.0, completed Jun. 5, 2014 and dated Jun. 16, 2014; (5 pp).

(Continued)

*Primary Examiner* — Joseph S Del Sole
*Assistant Examiner* — Mohamed K Ahmed Ali (57) ABSTRACT

A bimodal spinneret system including the bimodal spinneret and method for making a surgical buttress having improved characteristics are disclosed. The bimodal spinneret includes at least a distribution of hole diameters to create fibers with a more heterogeneous shear history and die swell. The system and method of using the bimodal spinneret creates a melt blown non-woven fiber mat that is cut into a surgical buttress having unique fabric properties such as differentiated load deflection behavior, flexural stiffness, polymer fiber alignment, fiber crystallinity and subsequent strength retention during in vitro degradation not attainable with unimodal spinneret hole diameters.

20 Claims, 5 Drawing Sheets

(56) References Cited

U.S. PATENT DOCUMENTS

| | | | |
|---|---|---|---|
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Duncan et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,266,255 A * | 11/1993 | Gibbon ................ D01D 4/02 264/210.7 |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,319,865 B1 | 11/2001 | Mikami |
| 6,325,810 B1 | 12/2001 | Hamilton et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,590,095 B1 | 7/2003 | Schleicher et al. |
| 6,592,597 B2 | 7/2003 | Grant et al. |
| 6,605,294 B2 | 8/2003 | Sawhney |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,009,034 B2 | 3/2006 | Pathak et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,141,055 B2 | 11/2006 | Abrams et al. |
| 7,147,138 B2 | 12/2006 | Shelton, IV |
| 7,160,299 B2 | 1/2007 | Baily |
| 7,232,449 B2 | 6/2007 | Sharkawy et al. |
| 7,241,300 B2 | 7/2007 | Sharkawy et al. |
| 7,247,338 B2 | 7/2007 | Pui et al. |

(56) References Cited

U.S. PATENT DOCUMENTS

| | | |
|---|---|---|
| 7,279,322 B2 | 10/2007 | Pui et al. |
| 7,294,357 B2 | 11/2007 | Roby |
| 7,307,031 B2 | 12/2007 | Carroll et al. |
| 7,311,720 B2 | 12/2007 | Mueller et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,649,089 B2 | 1/2010 | Kumar et al. |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 7,989,371 B2 | 8/2011 | Angadjivand et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,028,883 B2 | 10/2011 | Stopek |
| 8,033,483 B2 | 10/2011 | Fortier et al. |
| 8,038,045 B2 | 10/2011 | Bettuchi et al. |
| 8,062,330 B2 | 11/2011 | Prommersberger et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,192,460 B2 | 6/2012 | Orban, III et al. |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,348,126 B2 | 1/2013 | Olson et al. |
| 8,348,130 B2 | 1/2013 | Shah et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |
| 8,408,440 B2 | 4/2013 | Olson et al. |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,631,989 B2 | 1/2014 | Aranyi et al. |
| 8,668,129 B2 | 3/2014 | Olson |
| 8,684,250 B2 | 4/2014 | Bettuchi et al. |
| 8,757,466 B2 | 6/2014 | Olson et al. |
| 8,789,737 B2 | 7/2014 | Hodgkinson et al. |
| 8,820,606 B2 | 9/2014 | Hodgkinson |
| 9,266,046 B2 | 2/2016 | Kuroda et al. |
| 2001/0000189 A1* | 4/2001 | Hayes ............... A61L 31/06 |
| | | 623/23.75 |
| 2002/0028243 A1 | 3/2002 | Masters |
| 2002/0086990 A1 | 7/2002 | Kumar et al. |
| 2002/0091397 A1 | 7/2002 | Chen |
| 2003/0065345 A1 | 4/2003 | Weadock |
| 2003/0078209 A1 | 4/2003 | Schmidt |
| 2003/0083676 A1 | 5/2003 | Wallace |
| 2003/0120284 A1 | 6/2003 | Palacios et al. |
| 2003/0181927 A1 | 9/2003 | Wallace |
| 2003/0183671 A1 | 10/2003 | Mooradian et al. |
| 2003/0208231 A1 | 11/2003 | Williamson et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0131225 A1 | 6/2005 | Kumar et al. |
| 2005/0149073 A1 | 7/2005 | Arani et al. |
| 2005/0154093 A1 | 7/2005 | Kwon et al. |
| 2006/0004407 A1 | 1/2006 | Hiles et al. |
| 2006/0008505 A1 | 1/2006 | Brandon |
| 2006/0093672 A1 | 5/2006 | Kumar et al. |
| 2006/0121266 A1 | 6/2006 | Fandel et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0054880 A1 | 3/2007 | Saferstein et al. |
| 2007/0057414 A1* | 3/2007 | Hartge ............... D04H 3/005 |
| | | 264/555 |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0213522 A1 | 9/2007 | Harris et al. |
| 2007/0237741 A1 | 10/2007 | Figuly et al. |

(56) References Cited

U.S. PATENT DOCUMENTS

| | | |
|---|---|---|
| 2007/0237742 A1 | 10/2007 | Figuly et al. |
| 2007/0246505 A1 | 10/2007 | Pace-Floridia et al. |
| 2008/0026659 A1 | 1/2008 | Brandner et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0164440 A1 | 7/2008 | Maase et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0194805 A1 | 8/2008 | Vignon et al. |
| 2008/0200949 A1 | 8/2008 | Hiles et al. |
| 2008/0214695 A1 | 9/2008 | Pathak et al. |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0220560 A1 | 9/2009 | Wan et al. |
| 2009/0263441 A1 | 10/2009 | McKay |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0065660 A1 | 3/2010 | Hull et al. |
| 2010/0072254 A1 | 3/2010 | Aranyi et al. |
| 2010/0096481 A1 | 4/2010 | Hull et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0203151 A1 | 8/2010 | Hiraoka |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0082427 A1 | 4/2011 | Golzarian et al. |
| 2011/0087279 A1 | 4/2011 | Shah et al. |
| 2011/0089375 A1 | 4/2011 | Chan et al. |
| 2011/0215132 A1 | 9/2011 | Aranyi et al. |
| 2011/0293690 A1 | 12/2011 | Griffin et al. |
| 2012/0074199 A1 | 3/2012 | Olson et al. |
| 2012/0080336 A1 | 4/2012 | Shelton, IV et al. |
| 2012/0156289 A1 | 6/2012 | Blaskovich et al. |
| 2012/0187179 A1 | 7/2012 | Gleiman |
| 2012/0241499 A1 | 9/2012 | Baxter, III et al. |
| 2012/0273547 A1 | 11/2012 | Hodgkinson et al. |
| 2012/0315225 A1 | 12/2012 | Porbeni et al. |
| 2013/0037596 A1 | 2/2013 | Bear et al. |
| 2013/0105548 A1 | 5/2013 | Hodgkinson et al. |
| 2013/0105553 A1 | 5/2013 | (Tarinelli) Racenet et al. |
| 2013/0112732 A1 | 5/2013 | Aranyi et al. |
| 2013/0112733 A1 | 5/2013 | Aranyi et al. |
| 2013/0123816 A1 | 5/2013 | Hodgkinson et al. |
| 2013/0146641 A1 | 6/2013 | Shelton, IV et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze et al. |
| 2013/0181031 A1 | 7/2013 | Olson et al. |
| 2013/0193186 A1 | 8/2013 | (Tarinelli) Racenet et al. |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0209659 A1 | 8/2013 | Racenet et al. |
| 2013/0221062 A1 | 8/2013 | Hodgkinson |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0277411 A1 | 10/2013 | Hodgkinson et al. |
| 2013/0306707 A1 | 11/2013 | Viola et al. |
| 2013/0310873 A1 | 11/2013 | Stopek (nee Prommersberger) et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |
| 2014/0084042 A1 | 3/2014 | (Prommersberger) Stopek et al. |
| 2014/0097224 A1 | 4/2014 | Prior |
| 2014/0103556 A1 | 4/2014 | Diaz de Leon Izquierdo et al. |
| 2014/0117066 A1 | 5/2014 | Aranyi et al. |
| 2014/0130330 A1 | 5/2014 | Olson et al. |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek (nee Prommersberger) et al. |
| 2014/0166721 A1 | 6/2014 | Stevenson et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson et al. |
| 2014/0305090 A1 | 10/2014 | Kuroda et al. |

FOREIGN PATENT DOCUMENTS

| | | |
|---|---|---|
| EP | 0 327 022 A2 | 8/1989 |
| EP | 0 594 148 A1 | 4/1994 |
| EP | 0 667 119 A1 | 8/1995 |
| EP | 1 064 883 A1 | 1/2001 |
| EP | 1 256 317 A2 | 11/2002 |
| EP | 1 256 318 A1 | 11/2002 |

(56) References Cited

FOREIGN PATENT DOCUMENTS

| | | |
|---|---|---|
| EP | 1 520 525 A1 | 4/2005 |
| EP | 1 621 141 A2 | 2/2006 |
| EP | 1 702 570 A1 | 9/2006 |
| EP | 1 759 640 A2 | 3/2007 |
| EP | 1 815 804 A2 | 8/2007 |
| EP | 1 825 820 A1 | 8/2007 |
| EP | 1 929 958 A2 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 090 231 A1 | 8/2009 |
| EP | 2 090 244 A2 | 8/2009 |
| EP | 2 090 252 A2 | 8/2009 |
| EP | 2 198 787 A1 | 6/2010 |
| EP | 2 236 098 A2 | 10/2010 |
| EP | 2 236 099 A1 | 10/2010 |
| EP | 2 311 386 A2 | 4/2011 |
| EP | 2 436 348 A1 | 4/2012 |
| EP | 2 462 880 A2 | 6/2012 |
| EP | 2 517 637 A1 | 10/2012 |
| EP | 2 586 380 A1 | 5/2013 |
| EP | 2 604 195 A1 | 6/2013 |
| EP | 2 604 197 A2 | 6/2013 |
| EP | 2 620 106 A2 | 7/2013 |
| EP | 2 630 922 A1 | 8/2013 |
| EP | 2 644 125 A2 | 10/2013 |
| EP | 2 792 777 A1 | 10/2014 |
| JP | 02289107 | 11/1990 |
| JP | 05186240 | 7/1993 |
| JP | 08209432 | 8/1996 |
| JP | 11131353 | 5/1999 |
| JP | 2000-166933 A | 6/2000 |
| JP | 2001040566 A | 2/2001 |
| JP | 2002-202213 A | 7/2002 |
| JP | 2007-124166 A | 5/2007 |
| WO | 90/05489 A1 | 5/1990 |
| WO | 95/16221 A1 | 6/1995 |
| WO | 96/22055 A1 | 7/1996 |
| WO | 97/01989 A1 | 1/1997 |
| WO | 97/13463 A1 | 4/1997 |
| WO | 98/17180 A1 | 4/1998 |
| WO | 99/23285 A1 | 5/1999 |
| WO | 99/45849 A1 | 9/1999 |
| WO | 03/088845 A2 | 10/2003 |
| WO | 03082126 A1 | 10/2003 |
| WO | 03/094743 A1 | 11/2003 |
| WO | 03/105698 A2 | 12/2003 |
| WO | 2005079675 A2 | 9/2005 |
| WO | 2006023578 A2 | 3/2006 |
| WO | 2006044490 A2 | 4/2006 |
| WO | 2006083748 A1 | 8/2006 |
| WO | 2007121579 A1 | 11/2007 |
| WO | 2008057281 A2 | 5/2008 |
| WO | 2008109125 A1 | 9/2008 |
| WO | 2008085546 | 12/2008 |
| WO | 2010075298 A2 | 7/2010 |
| WO | 2011143183 A2 | 11/2011 |
| WO | 2012044848 A1 | 4/2012 |

OTHER PUBLICATIONS

Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
Extended European Search Report corresponding to counterpart Int'l Appln. No. EP 15 20 0068.3 dated Jun. 3, 2016.
European Search Report corresponding to EP 05 02 2585.3, completed Jan. 25, 2006 and dated Feb. 3, 2006; (4 pp).
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 10 25 1437.9, completed Nov. 22, 2010 and dated Dec. 16, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 11 18 8309.6, completed Dec. 15, 2011 and dated Jan. 12, 2012; (3 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013I; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).

(56) References Cited

OTHER PUBLICATIONS

Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
European Office Action corresponding to counterpart Int'l Application No. EP 15 20 0068.3 dated Sep. 8, 2017.
Chinese First Office Action corresponding to counterpart Patent Appln. CN 201510896261.0 dated Dec. 26, 2018.
Chinese Third Office Action dated Jul. 2, 2019 corresponding to counterpart Patent Application CN 201510896261.0.
Chinese Second Office Action corresponding to counterpart Patent Appln. CN 201510896261.0 dated Apr. 23, 2019.
Japanese Office Action dated Dec. 2, 2019 corresponding to counterpart Patent Application JP 2015-239080.
Australian Examination Report No. 1 dated Jun. 5, 2020 corresponding to counterpart Patent Application AU 2015252118.

\* cited by examiner

SPINNERET FOR MANUFACTURE OF MELT BLOWN NONWOVEN FABRIC

TECHNICAL FIELD

The present disclosure relates to surgical buttresses and equipment for their manufacture, and more particularly, to a spinneret configured to make a nonwoven fabric surgical implant or buttress created from a melt blown process.

BACKGROUND

Surgical stapling instruments that are used to sequentially or simultaneously apply one or more rows of fasteners to join segments of body tissues are well known in the art. Such devices generally include a pair of jaws to clamp therebetween the body tissues to be joined. Typically, one of the jaw members includes a staple cartridge which accommodates a plurality of staples while the other jaw member has an anvil that defines a surface for forming the staple legs as the staples are driven from the staple cartridge. When stapling relatively thin or fragile tissues, it is often necessary to reinforce the staple line against the tissue to prevent tears in the tissue or pulling of the staples through the tissue. One method of preventing tears or pull through involves the placement of a biocompatible fabric reinforcing material, or a "buttress," between the staple and the underlying tissue.

A common method for making a buttress is to extrude a biocompatible material through a spinneret having a unimodal distribution of hole diameters to form fibers, collect the fibers to create a fiber mat and then cut the nonwoven fiber mat into a predetermined shape. However, using a spinneret with a unimodal distribution of hole diameters produces a buttress having a certain flexibility and strength.

It is a desire of the present application to provide a spinneret, system and method for making a nonwoven fiber mat that results in a buttress having improved flexibility and strength characteristics.

Specifically, this disclosure presents a spinneret design that includes at least a distribution of hole diameters to create fibers with a more heterogeneous shear history and die swell. All of these advantages confer unique fabric properties not attainable with unimodal spinneret hole diameters such as differentiated load deflection behavior, flexural stiffness, polymer fiber alignment, fiber crystallinity and subsequent strength retention during in vivo degradation.

SUMMARY

In accordance with aspects of the present disclosure, a multi-modal spinneret is provided, including a body defining a longitudinal axis, wherein the body includes a first side surface and a second side surface, and a top surface and a bottom surface; and at least two holes disposed along the longitudinal axis of the spinneret, each of the at least two holes having a hole diameter, wherein at least one hole has a first diameter and least one hole has a second diameter different than the first diameter.

The spinneret can include additional holes, and wherein each of the additional holes has a hole diameter equivalent to either the first or second diameter. The additional holes of the spinneret may be disposed along the longitudinal axis of the spinneret in a pattern of alternating first and second diameters or randomly disposed along the longitudinal axis of the spinneret. The number of holes having a first diameter and the number of holes having a second diameter may be equal.

In aspects, each of the additional holes has a center and an edge, the additional holes may be disposed along the longitudinal axis of the spinneret such that the centers of the additional holes are equidistant or the distance between each edge of each of the additional holes are equidistant.

In aspects, the at least two holes of the spinneret have a hole depth, and wherein each of the at least two holes has a ratio that is defined by the hole depth divided by the hole diameter. Each of the ratios of the at least two holes may be equal or unequal.

In accordance with another aspect of the present disclosure, a method of making a nonwoven fiber mat is disclosed and comprises providing a material, an extruder and a spinneret, wherein the spinneret defines at least one hole having one diameter and at least one hole having a second diameter different than the first diameter; coupling the spinneret to the extruder; feeding the material into the extruder; melting the material in the extruder; extruding the melted material through the spinneret forming a plurality of fibers; and collecting the plurality of fibers onto a conveyer surface to form a nonwoven fiber mat, wherein the nonwoven fiber mat includes at least one fiber having a first diameter and at least one fiber having a second diameter.

In certain embodiments, the material is a polymer selected from the group consisting of lactide homopolymer, glycolide homopolymer, polydioxanone homopolymer, glycolide trimethylene carbonate copolymer, glycolide lactide copolymer, glycolide dioxanone trimethylene carbonate copolymer, and glycolide caprolactone trimethylene carbonate lactide copolymer.

In certain embodiments, the material is a bioabsorbable polymeric material. The melting temperature of the polymer may be between about 180 and about 270 degrees Celsius. In other embodiments, the melting temperature of the polymer is between about 80 degrees Celsius and about 190 degrees Celsius.

The method may also include blowing hot air on the plurality of fibers as they exit the spinneret and before they are collected on the conveyer surface. The hot air may have a temperature greater than or equal to the melting temperature of the plurality of fibers. The hot air may have a temperature of between about 225 and about 290 degrees Celsius. The hot air may have a temperature of about 240 degrees Celsius.

In certain embodiments, the method includes plasma treating at least a portion of a surface of the non-woven fiber mat with an ionizable gas species or combination of ionizable gas species configured to chemically modify or functionalize the surface of the non-woven fiber mat. The ionizable gas species is selected from the group consisting of air, water vapor, oxygen, nitrogen, argon, and combinations thereof.

In certain embodiments, the method includes applying heat and pressure to the non-woven fiber mat before plasma treating the non-woven fiber mat.

In certain embodiments, the non-woven material is cut into a shape corresponding to the shape of the tissue contacting surfaces of a linear surgical stapler. In other embodiments, the non-woven material is cut into a shape corresponding to the shape of the tissue contacting surfaces of a circular surgical stapler.

In accordance with another aspect of the present disclosure, a system for making a surgical buttress for surgical staplers is disclosed and comprises an extruder configured to receive and melt a material; a spinneret coupled to the extruder and configured to form a plurality of fibers, wherein the spinneret defines at least two holes of different sizes; and a conveyer surface configured to receive the plurality of fibers extruded from the spinneret. The extruder may reach a temperature between about 180 and about 270 degrees Celsius or temperatures between about 80 degrees Celsius and about 190 degrees Celsius. The system may include a blower and/or compressed air, wherein the blower and/or compressed air blows hot air on the plurality of fibers as they exit the spinneret.

In certain embodiments, the hot air from the blower and/or compressed air may have a temperature greater than or equal to the melting temperature of the plurality of fibers. The hot air may have a temperature approximately between 225 and 290 degrees Celsius.

In certain embodiments, the system may include a plasma treatment apparatus, wherein the plasma treatment apparatus treats at least a portion of a surface of the non-woven fiber mat with an ionizable gas species or combination of ionizable gas species configured to chemically modify or functionalize the surface of the non-woven fiber mat. The ionizable gas species is selected from the group consisting of air, water vapor, oxygen, nitrogen, argon, and combinations thereof.

In certain embodiments, the system may include a cutting apparatus to cut the nonwoven fiber mat into a buttress. The non-woven fiber mat is cut into a shape corresponding to the shape of the tissue contacting surfaces a linear surgical stapler or into a shape corresponding to the shape of the tissue contacting surfaces a circular surgical stapler.

BRIEF DESCRIPTION OF THE DRAWINGS

The foregoing objects and advantages of the disclosure will become more apparent from the reading of the following description in connection with the accompanying drawings, in which.

DETAILED DESCRIPTION

The present disclosure is directed to a spinneret design, system and method of using a melt blown process to make a nonwoven fiber mat having a distribution of fiber diameters.

For the purposes of discussion, the nonwoven fiber mat will be discussed in terms of a surgical buttress. However, those skilled in the art will appreciate the presently disclosed nonwoven fiber mat may be any surgical implant, such as meshes, scaffolds, grafts (e.g., fabrics and/or tubes), rings, sutures, patches, slings, pledgets, growth matrices, drug delivery devices, wound plugs, and, in general, soft tissue repair devices and surgical prostheses. In other embodiments, a suitable nonwoven fiber mat may be cut as topically applied medical products, such as wound dressings, coverings, gauzes, and the like, that can be used in medical/surgical procedures.

Figure 1:
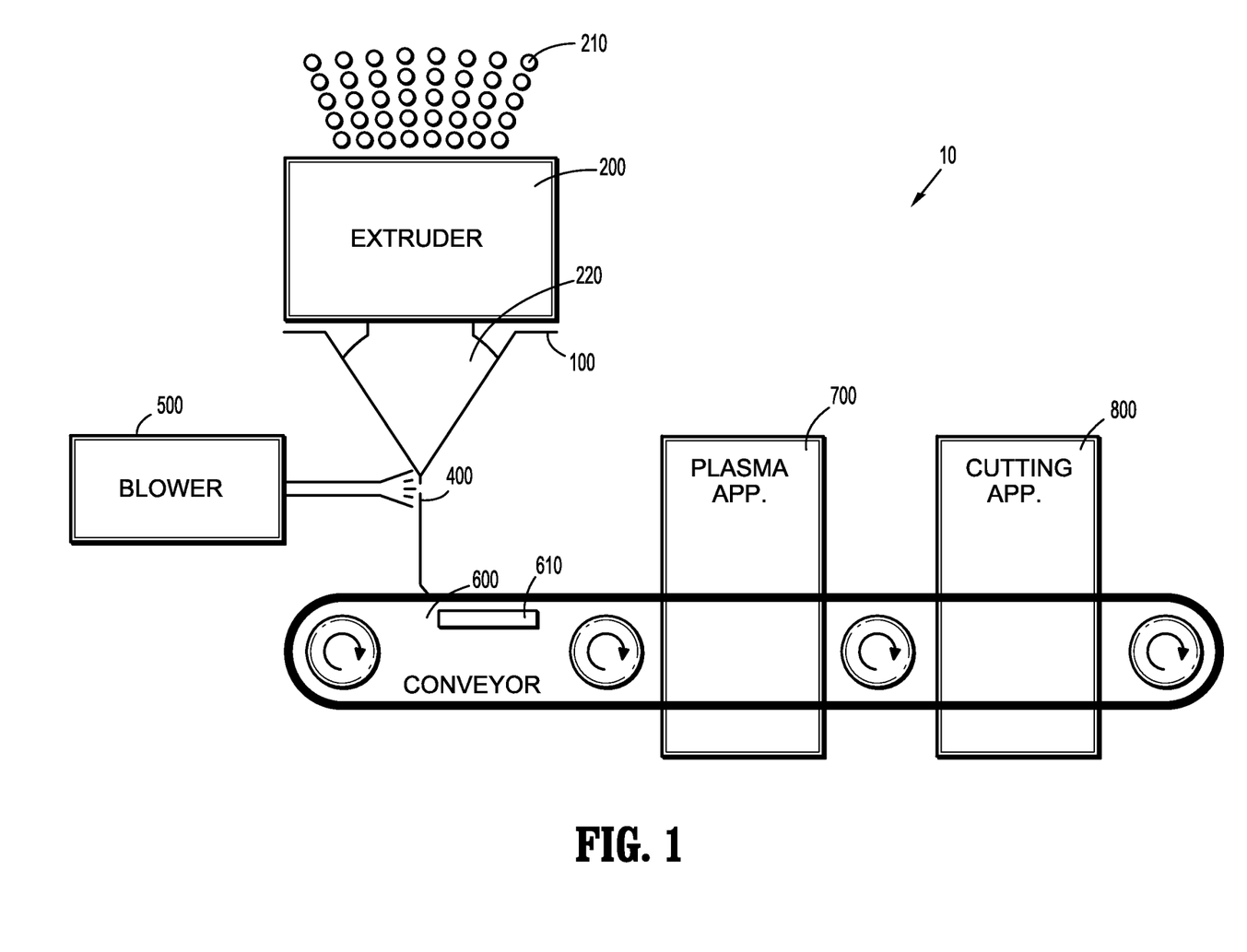
FIG. 1 is a schematic illustration of a system for making a surgical buttress according to the present disclosure.

Referring now to the figures, wherein like components are designated by like reference numerals throughout the several views, With reference to FIG. 1, a system for making a surgical buttress material, is generally designated as 10. As will be discussed in greater detail below, system 10 generally includes a bimodal spinneret 100, an extruder 200 configured to supply material 210 to spinneret 100, a blower and/or compressed air 500 configured to blow hot air onto fibers 400 and transport fibers 400 to a plasma apparatus 700 and then onto a cutting apparatus 800.

Figure 2:
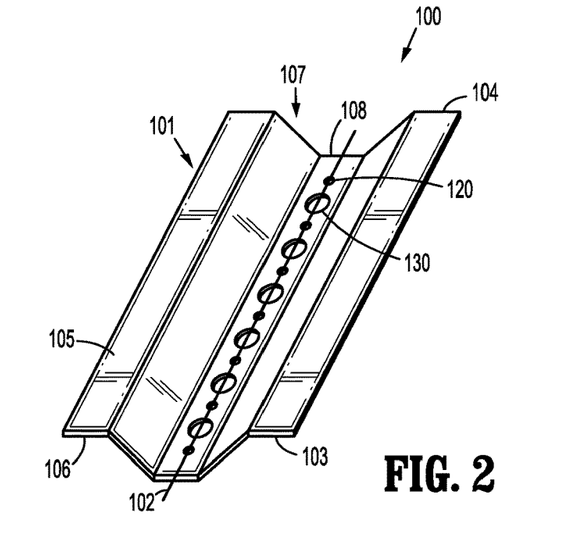
FIG. 2 is a perspective view of a spinneret, in accordance with an embodiment of the present disclosure, for use in the system of FIG. 1.

FIG. 2 illustrates a perspective view of a spinneret 100 in accordance with one embodiment of the present disclosure. Spinneret 100 includes a body portion 101 defining a longitudinal axis 102 extending from a proximal end 103 to a distal end 104 of the body portion 101. Preferably, spinneret 100 may have a substantially V-shaped profile, however spinneret 100 may be any other suitable shape. The body portion further defines a cavity 107 defining a nadir 108 that is formed along the longitudinal axis 102 of the body portion 101. Disposed along longitudinal axis 102 of body portion 101 are at least two through holes 120,130. Through hole 120 has a first diameter "D1" and through hole 130 has a second diameter "D2" that is different from first diameter "D1". First diameter "D1" may be more than 100% larger than second diameter "D2". Optimally, the size difference between first and second diameters "D1", "D2" is at least 10%. Generally, the first and second diameters "D1", "D2" range from about 0.13 mm to about 0.3 mm, in some embodiments, from about 0.175 mm to about 0.25 mm. Spinneret 100 may be composed of steel, however any other suitable material may be used.

Figure 3:
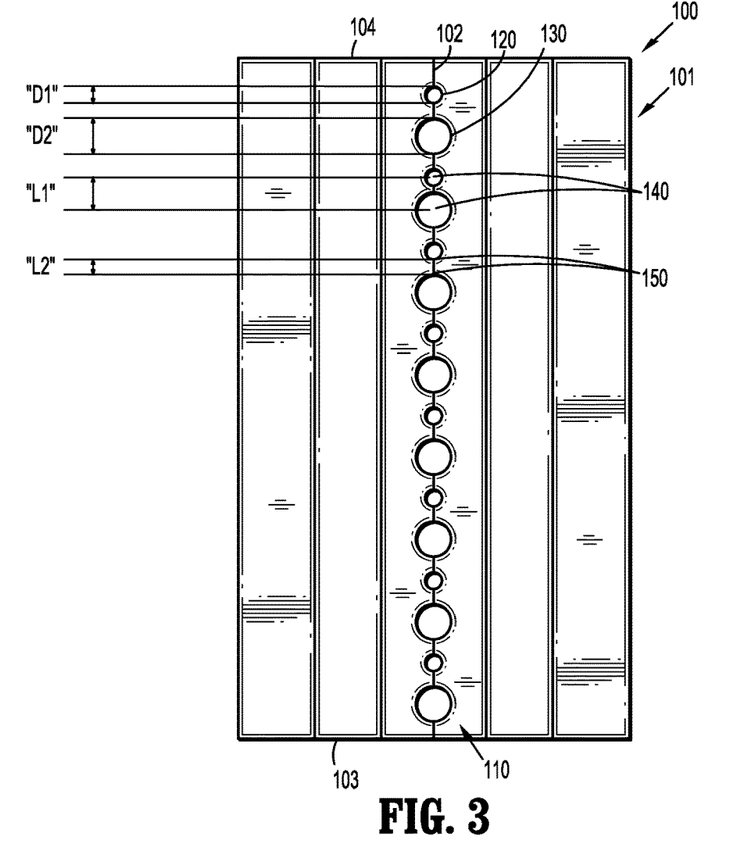
FIG. 3 is a bottom view of the spinneret of FIG. 2.

FIG. 3 illustrates a bottom view of spinneret 100. In an embodiment, the body portion 101 of spinneret 100 has a plurality of holes 110, where the plurality of holes 110 includes through holes 120, 130. Each of the holes 110 has a diameter equal to either the first or second diameter "D1", "D2". Holes 110 are disposed along longitudinal axis 102 in an alternating pattern such that a hole having first diameter "D1" is next to a hole having a second diameter "D2". Alternatively, holes 110 may be disposed along longitudinal axis 102 in a random pattern (not shown) or any pattern desired.

Still referring to FIG. 3, each of the holes 110 is circular, having a center 140 and a side edge 150. Each hole 110 may be disposed along longitudinal axis 102 such that a distance "L1" between each center 140 is equal. Alternatively, each hole 110 may be disposed along longitudinal axis 102 such that a distance "L2" between each side edge 150 is equal.

Figure 4:
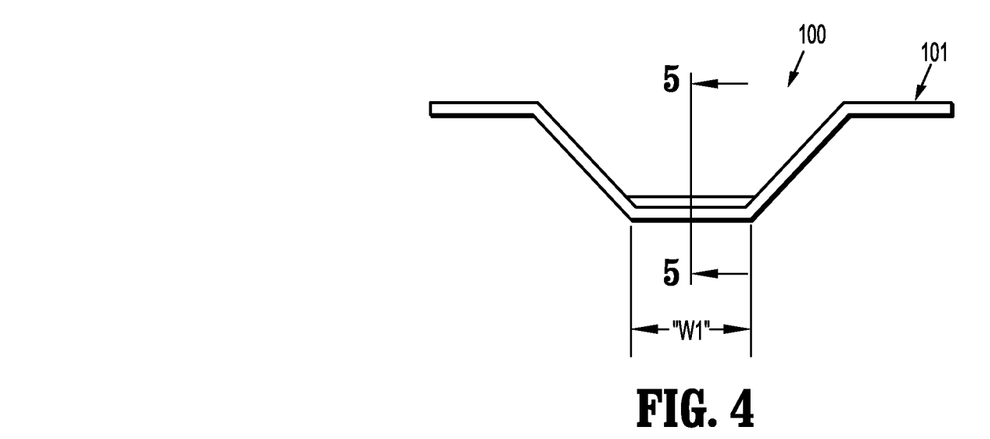
FIG. 4 is a front, elevational view of the spinneret of FIG. 2.

Turning to FIG. 4, the nadir 108 of spinneret 100 may be substantially flat and dimensioned such that the width "W1" is greater than each of the holes 110.

Figure 5:
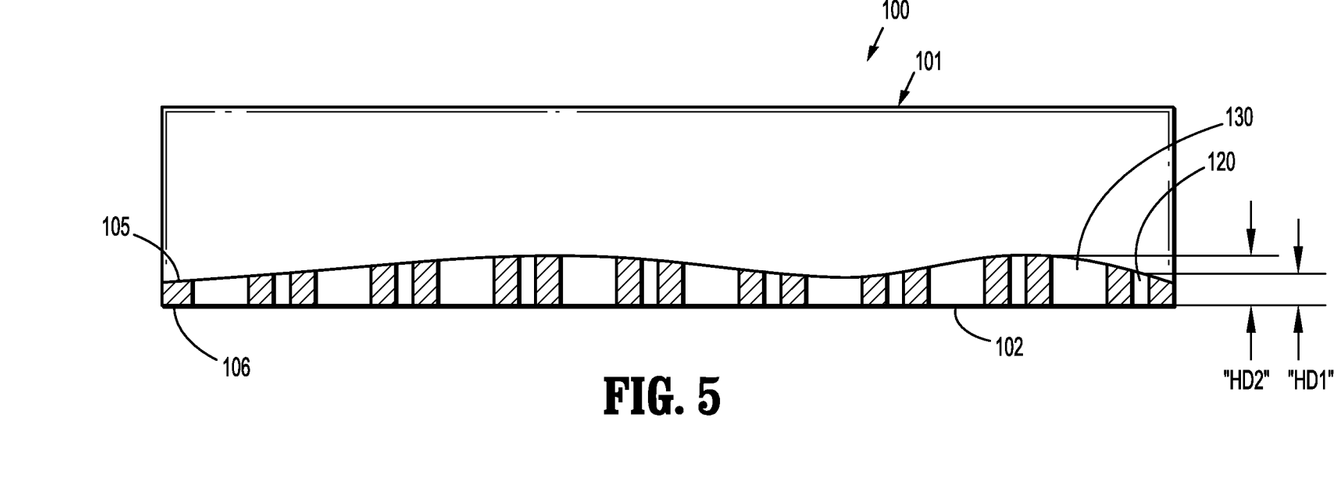
FIG. 5 is a cross-sectional of the spinneret of FIGS. 2 and 3, as taken along 5-5 or FIG. 4.

Shown in FIG. 5 is a cross-sectional view of spinneret 100 as taken along cross-sectional line 5-5 of FIG. 4. Each of the holes 110 has a hole depth extending from a top surface 105 to a bottom surface 106 of the body portion 110. Preferably, each hole depth is different; however, each hole depth may be the same. Here, through hole 120 has a hole depth "HD1" and through hole 130 has a hole depth "HD2" that is greater than "HD1."

Referring back to FIG. 1, as mentioned above, spinneret 100 is operatively connected to extruder 200. Extruder 200 is configured to receive material 210 therein from a supply source (not shown). Material 210 may include polymers such as those made from lactide, glycolide, caprolactone, valerolactone, carbonates (e.g., trimethylene carbonate, tetramethylene carbonate, and the like), dioxanones (e.g., 1,4-dioxanone), δ-valerolactone, 1,dioxepanones (e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, poly (ortho esters), hydroxy alkanoates, tyrosine carbonates, poly (imide carbonates), poly(imino carbonates) such as poly (bisphenol A-iminocarbonate) and poly (hydroquinone-iminocarbonate), polyurethanes, polyanhydrides, polymer drugs (e.g., polydiflunisol, polyaspirin, and protein therapeutics), and copolymers and combinations thereof.

In embodiments, material 210 may be a lactomer copolymer of glycolide and lactide derived from glycolic and lactic acids. In embodiments, the porous nonwoven fiber mat may be fabricated from polyglyconate, a copolymer of glycolic acid and trimethylene carbonate.

In other embodiments, material 210 may be a synthetic polyester composed of glycolide, dioxanone, and trimethylene carbonate. The polymer may include from about from about 50% to about 70% by weight glycolide, in embodiments, from about 55% to about 65% by weight glycolide, and in some embodiments, about 60% by weight glycolide; from about 4% to about 24% by weight dioxanone, in embodiments, from about 9% to about 19% by weight dioxanone, and in some embodiments, about 14% by weight dioxanone; and from about 16% to about 36% by weight trimethyl carbonate, in embodiments, from about 21% to about 31% by weight trimethyl carbonate, and in some embodiments, about 26% by weight trimethyl carbonate.

In yet other embodiments, material 210 may be a copolymer of glycolide and trimethylene carbonate. The polymer may include from about 55% to about 75% by weight glycolide, in embodiments, about 60% to about 70% by weight glycolide, and in some embodiments, about 65% by weight glycolide, and from about 25% to about 45% by weight trimethylene carbonate, in embodiments, from about 30% to about 40% by weight trimethylene carbonate, and in some embodiments, about 35% by weight trimethylene carbonate.

Extruder 200 is configured to heat material 210 until it becomes a melted material 220, and then forces melted material 220 into spinneret 100 and through the array of holes therein. In some embodiments, the temperature of spinneret 100 is between about 200 degrees Celsius, and about 275 degrees Celsius in some embodiments, from between about 235 degrees Celsius and about 255 degrees Celsius. In some embodiments, the pressure, at spinneret 100, acting on melted material 220, is between about 10 bar and about 80 bar. In some embodiments, the pressure can be 125 bar.

Spinneret 100 forms melted material 220 into fibers 400 having differing fiber diameters. Blower and/or compressed air 500 blows hot air onto fibers 400 exiting spinneret 100 to force fibers 400 onto a conveyor surface 600. In some embodiments, the hot air has a temperature of between about 225 degrees Celsius and about 325 degrees Celsius, and in other embodiments hot air has a temperature from about 265 degrees Celsius and about 295 degrees Celsius. The speed of conveyor surface 600 is between about 1 meter per minute and about 10 meters per minute. Fibers 400 randomly land on conveyor surface and build up to several layers in thickness. Suction 610 is applied through conveyor surface 600 to help compact fibers 400 against each other to form a nonwoven fiber mat 410 as fibers 400 cool.

It is contemplated that fibers 400 can be generated at lower temperatures. In certain embodiments, fibers 400 are formed from a material 210 having a lower melting temperature. For example, a copolymer of glycolide, caprolactone, trimethylene carbonate and lactide could be melt extruded at between about 140 degrees Celsius and about 185 degrees Celsius. Thus, the nonwoven fiber mat 410 may be formed from fibers 400 that are melt extruded from polymers having a melting temperature of between about 80 degrees Celsius and about 190 degrees Celsius.

The diameter of the individual fibers 400 may be from about 5 µm to about 100 µm in embodiments, from about 10 µm to about 40 µm in some embodiments, and from about 15 µm to about 35 µm in some embodiments, and in some further embodiments, from about 18 µm to about 33 µm. The nonwoven fiber mat 410 thickness may be from about 100 µm to about 400 µm in embodiments, and from about 100 µm to about 300 µm in some embodiments, and from about 200 µm to about 250 microns in some embodiments, and in some further embodiments about 230 µm. The nonwoven fiber mat 410 weight may be from about 75 $g/m^2$ to about 100 $g/m^2$, in embodiments, from about 80 $g/m^2$ to about 95 $g/m^2$, and in some embodiments, about 87 $g/m^2$. It should be understood that different mat thicknesses, weights, and porosities may be selected by varying manufacturing conditions. In certain embodiments, the fabric can be between 35 to 80 $g/m^2$.

In accordance with the present disclosure, the nonwoven fiber mat 410 may be chemically modified to render at least a portion of a surface of nonwoven fiber mat 410 hydrophilic. For example, in embodiments, the nonwoven fiber mat 410 is carried on conveyer surface 600 and delivered to a plasma apparatus 700 where a plasma treatment is used. The plasma may be formed of a single gas species such as oxygen, carbon dioxide, ammonia, nitrogen, or argon. The use of oxygen, for example, will result in surface activation of an oxygenate type, such as the formation of —OH, —CHO, and/or —COOH groups. It is envisioned that other gases, mixtures of gases, vapours of volatile organic molecules such as alcohols, water, or open air plasma may also be utilized. For example, ozone may be used in place of oxygen. In other examples, the plasma gas may be produced using an oxygen-containing molecule, a nitrogen-containing molecule, or mixtures thereof. In some embodiments, plasma gases may be used serially.

Once fiber mat 410 is plasma treated, nonwoven fiber mat 410 is carried on conveyor surface 600 and delivered to a cutting apparatus 800. Cutting apparatus 800 cuts nonwoven fiber mat 410 into a surgical buttress having a profile corresponding to a linear or circular stapling instrument.

Figure 6:
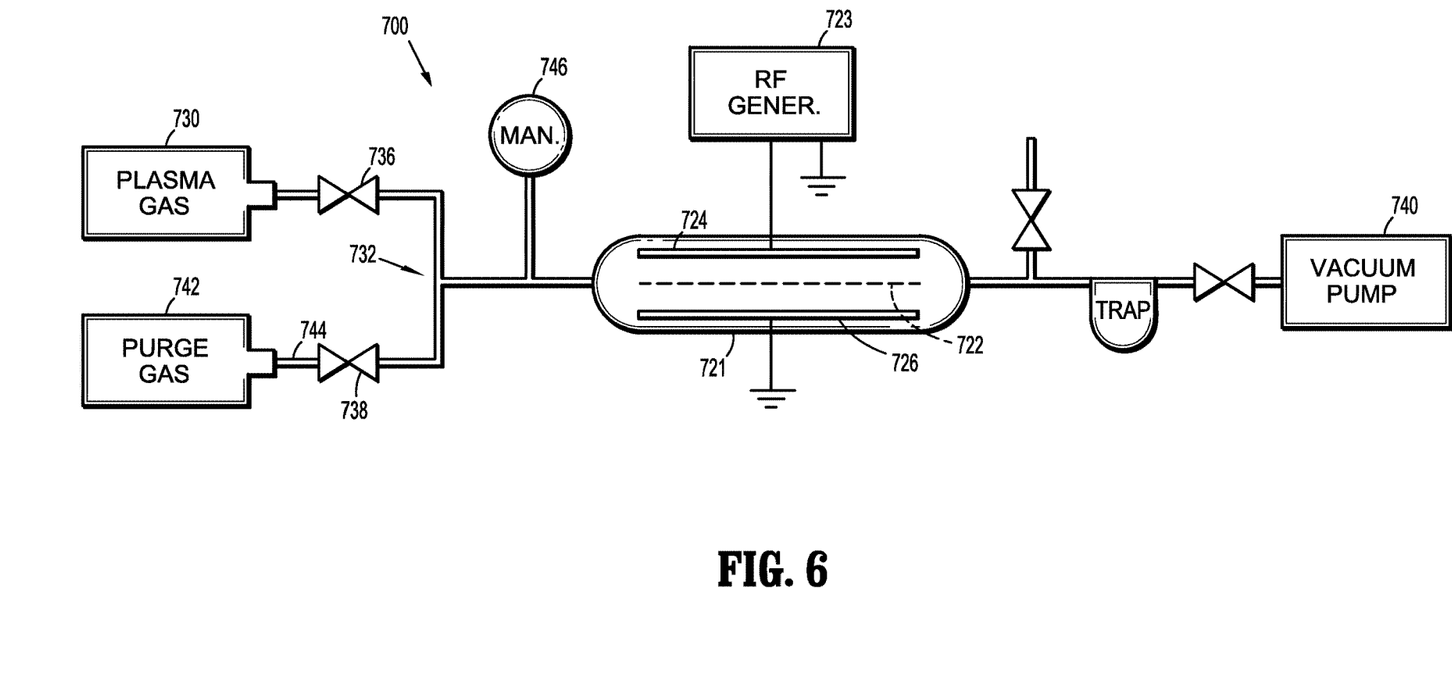
FIG. 6 is a schematic illustration of an apparatus which is suitable for carrying out plasma treatment of a nonwoven fiber mat in accordance with the present disclosure.

An illustrative plasma apparatus is shown in FIG. 6. Plasma apparatus 700 includes a chamber 721 including a rack 722, such as a stainless steel rack, and a pair of parallel electrode plates 724 and 726 between which a plasma is formed. A radio frequency generator 723 is provided as a source of potential, with an output terminal of the generator 723 being connected to electrode plate 724 and electrode plate 726 being grounded, thereby providing means for generating an electrical field between the electrode plates 724 and 726, in which field the plasma can be created and sustained. To provide the desired gas from which the plasma is formed, the apparatus 700 includes a plasma gas source 730 (typically a standard gas cylinder) connected through a gas inlet system 732 to the chamber 721. The plasma gas source 730 includes a valve 736 for controlling the flow of gas through a supply line 734. A purge gas source 742, such as helium, is also connected through a line 744 and valve 738 to gas inlet system 732. A vacuum pump 740 is connected to the chamber 721 for reducing the gas pressure therein.

Preferably, the nonwoven fiber mat 410 may travel through the plasma field between reels in a continuous reel to reel system requiring no support rack. Alternatively, the nonwoven fiber mat 410 is mounted within the chamber 721 on the rack 722, positioned between electrode plates 724 and 726. Alternatively, the rack 722 may be movable so that nonwoven fiber mat 410 may be pulled through the chamber 721. The gas inlet system 732 is operated to permit reacting gas monomer from plasma gas source 730 to flow into the chamber 721 through the supply line 734 before generating a plasma.

The plasma is created by applying the output of the radio frequency generator 723 to the electrode plate 724. The power supplied by the generator 723 is at the minimum required to sustain the plasma, as higher powered plasma will only degrade the surface of nonwoven fiber mat 410. The reaction between the plasma and nonwoven fiber mat 410 is allowed to proceed for a period of time determined by the desired thickness and surface energy on nonwoven fiber mat 410 and the concentration of gas monomers in the reacting vapor. The pressure within the chamber 721 is measured by a capacitance manometer 746 to maintain appropriate pressure throughout the reaction period.

Following the reaction period, the flow of gas from the plasma gas source 730 is terminated, the power from the generator 723 sustaining the plasma is turned off, and valve 738 is opened to permit gas to flow into the chamber 721 from purge gas source 742 to purge nonwoven fiber mat 410 surface of highly reactive radicals which could cause premature contamination of nonwoven fiber mat's 410 surface. Valve 838 is then closed, the chamber 721 is opened so that chamber 721 is returned to atmospheric pressure, and the plasma treated nonwoven fiber mat 410 is removed.

The plasma treated nonwoven fiber mat 410 may then be sterilized by any means within the purview of those skilled in the art including, but not limited to, ethylene oxide, electron beam, gamma irradiation, autoclaving, plasma sterilization, and the like.

It should be understood that the conditions under which treatment occurs may be dependent upon a number of factors, such as the type, size, thickness, and porosity of material being treated, the type and concentration of gas species being utilized and the flow rate thereof, the plasma technology system being utilized, and plasma treatment conditions such as voltage, pressure, temperature, duration, and the like.

For example, the plasma may include from about 1% to about 100% by weight of oxygen, nitrogen, or argon, in embodiments, from about 15% to about 90% by weight of oxygen, nitrogen, or argon, and in some embodiments, from about 25% to about 75% by weight oxygen, nitrogen, or argon. The gas may have a mass flow rate of from about 10 sccm to about 200 sccm, in embodiments, from about 25 sccm to about 150 sccm, and in some embodiments, about 50 sccm to about 100 sccm. The plasma generating electrodes may operate at a power of about 25 watts to about 1000 watts, in embodiments, from about 50 watts to about 750 watts, and in some embodiments, about 100 watts to about 500 watts. The treatment pressure may be about 25 mtorr to about 500 mtorr, in embodiments, from about 50 mtorr to about 400 mtorr, and in some embodiments, from about 100 mtorr to about 250 mtorr. The treatment may occur at a temperature of less than 100° C., and, in embodiments, at ambient temperature. The length of exposure may range from about 10 seconds to about 120 minutes, in embodiments, from about 30 seconds to about 60 minutes, and in some embodiments, from about 2 minutes to about 30 minutes. It will be appreciated by those skilled in the art that the treatment conditions may be outside the ranges set forth as discussed above.

In embodiments, the nonwoven fiber mat 410 treated in accordance with the present disclosure may also be subjected to a plasma polymerization process to form a polymer coating on at least a portion of the surface of nonwoven fiber mat 410. Such methods are disclosed, for example, in U.S. Pat. No. 7,294,357 and U.S. Patent Application Publication No. 2013/0123816 the entire contents of which are incorporated herein by reference.

The monomers used to form the polymer coating may be polymerized directly on nonwoven fiber mat's 410 surface using plasma-state polymerization techniques generally known to those skilled in the art. In brief, the monomers are polymerized onto the surface of nonwoven fiber mat 410 by activating the monomer in a plasma state. The plasma state generates highly reactive species, which form a highly cross-linked and highly-branched ultra-thin polymer coating, which is deposited on the surface of nonwoven fiber mat 410 during plasma polymerization.

In embodiments, a suitable organic monomer or a mixture of monomers having polymerizable unsaturated groups is introduced into the chamber where it is fragmented and/or activated forming further excited species in addition to the activated plasma gases. The excited species and fragments of the monomer recombine upon contact with the surface of nonwoven fiber mat 410 to form a largely undefined structure which contains a complex variety of different groups and chemical bonds and forms a highly cross-linked polymer coating. If oxygen, nitrogen, argon, or molecules possessing these elements are present, either within the plasma reactor during the polymer coating process or on exposure of the polymer coated nonwoven fiber mat 410 to oxygen or air subsequent to the plasma process, the polymeric deposit will include a variety of polar groups.

In embodiments, plasma polymerization may utilize solvents such as diglyme and tetraglyme, to produced PEG-like surfaces. In other embodiments, plasma polymerization may utilize fluorochemicals such as aliphatic fluorine-containing gases, to produced fluorinated polymer surfaces.

The amount and relative position of polymer deposition on the nonwoven fiber mat 410 is influenced by at least three geometric factors: (1) location of the electrode plates and distribution of charge; (2) monomer flow; and (3) nonwoven fiber mat 410 position within the chamber. In practice, an electric discharge from the RF generator may be applied to the electrode plates within the chamber and the selected monomers may be introduced into the chamber and energized into a plasma, saturating the space between the electrode plates with an abundance of energetic free radicals and lesser amounts of ions and free electrons produced by the monomers. As nonwoven fiber mat 410 is passed through, or positioned between, the electrode plates, the surface of nonwoven fiber mat 410 is bombarded with free radicals, resulting in the formation of the polymer coating.

In embodiments, siloxane monomers with hydrophilic end groups may be used in the plasma polymerization process to produce polymer coatings on the surface of nonwoven fiber mat 410. In some embodiments, aliphatic hydrocyclosiloxane monomers, alone or mixed with co-monomers, may be utilized to provide polymer coatings having a homogenous or mixed property coating. For example, by introducing reactive functionalizing monomers, organo-based monomers, or fluorocarbon monomers together with the aliphatic hydrocyclosiloxane monomers in the plasma polymerization system, physical pore size and chemical affinity of the plasma copolymerized aliphatic hydrocyclosiloxane coating with selective monomers can be controlled. This allows the use of the copolymerized plasma polymer coating for applications which require the coating to differentiate between certain types of gases, ions, and molecules and it also may be utilized to introduce functional groups to the polymer coating which, in turn, can help link hydrophilic molecules to the polymer coating.

Figure 7:
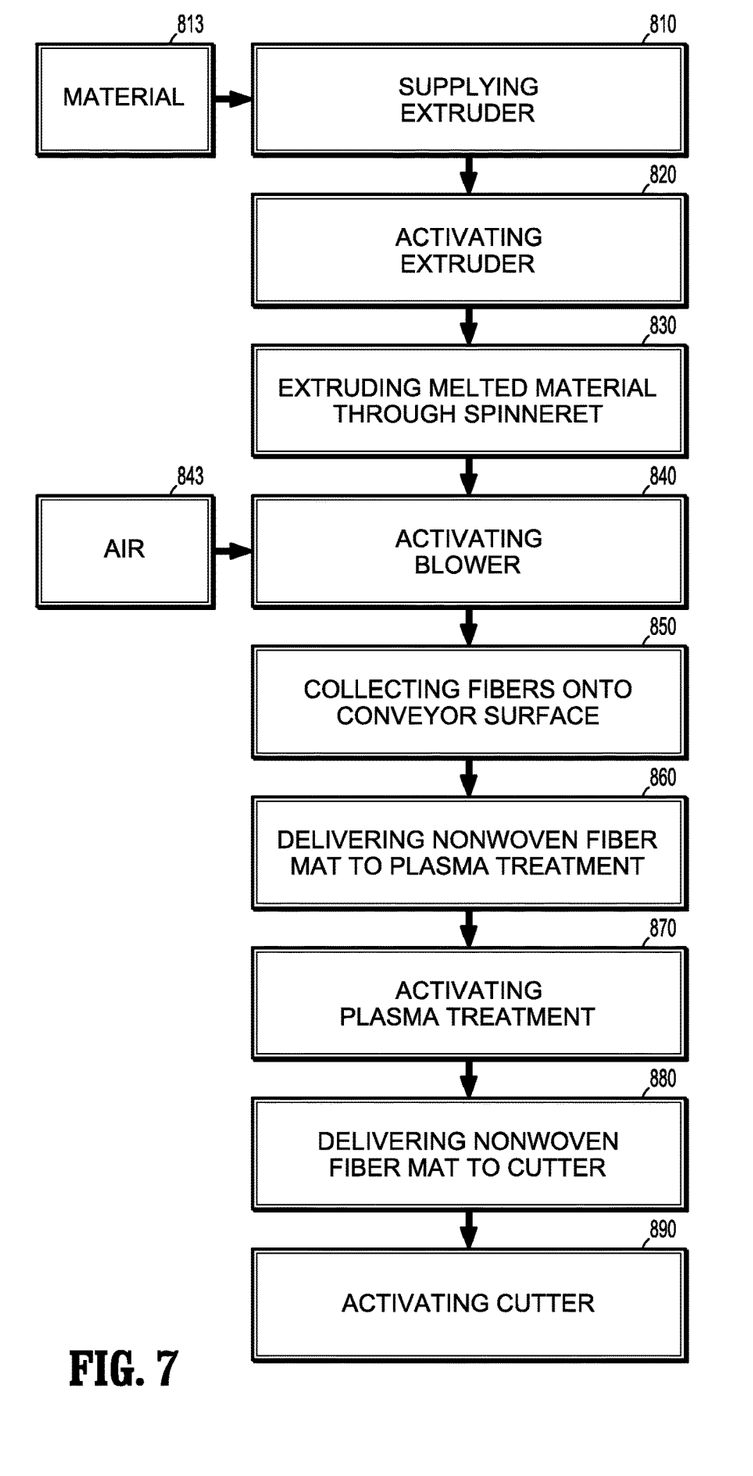
FIG. 7 is a flow chart illustrating a method of making a nonwoven fiber mat.

Referring now to FIG. 7, the use and operation of spinneret 100 in a system for making a nonwoven fiber mat is detailed. Although detailed with respect to spinneret 100 and system 10 of FIG. 1 for exemplary purposes, the system detailed herein is equally applicable for use with other spinnerets for making a nonwoven fiber mat.

Initially, as indicated in step 810, the extruder 200 is supplied with an appropriate amount of a material 210. Next, extruder 200 is activated. Once activated, as indicated in step 820, extruder 200 heats material 210 until it changes into melted material 220. Extruder 200 then proceeds to force melted material 220 through the array of holes 110 (See FIG. 3) in spinneret 100 thereby creating fibers 400, as indicated in step 830. Shown in steps 840 and 843, blower and/or compressed air 500 is activated and blows hot air onto fibers 400 as they exit spinneret 100. The air blown fibers 400 then collect onto conveyor surface 600 and cool to form a non-woven fiber mat 410, as indicated in step 850. As previously discussed, conveyor surface 600 includes a suction 610 to pull fibers 400 together as they cool.

The method may also include plasma treating non-woven fiber mat 410. Indicated in step 860, non-woven fiber mat 410 is delivered to a plasma treatment apparatus 700. Delivery may be by conveyor surface 600 or manually. In step 870, plasma treatment apparatus 700 is activated thereby surface treating non-woven fiber mat 410. A detailed discussion of the operation of plasma treatment apparatus 700 is discussed with reference to FIG. 6. Following plasma treatment, as indicated in step 880, non-woven fiber mat 410 is delivered to cutting apparatus 800. In step 890, cutting apparatus 800 is then activated to cut non-woven fiber mat 410 into a surgical buttress having a profile corresponding to a linear or circular surgical stapling instrument. However, as mentioned above, those skilled in the art will appreciate the presently disclosed nonwoven fiber mat may be cut to form any surgical implant, such as meshes, scaffolds, grafts, and the like.

While several embodiments of the disclosure have been shown in the drawings, it is not intended that the disclosure be limited thereto, as it is intended that the disclosure be as broad in scope as the art will allow and that the specification be read likewise. For example, a bimodal spinneret has been disclosed, but multiple different diameter holes can be used in other embodiments. In any of the embodiments disclosed herein, the holes can be arranged in a pattern or randomly. The spacing may be equidistant or otherwise. In certain embodiments, techniques for injecting cold air to the molten polymer can be used and/or techniques for removing process heat from the system during fiber mat deposition can be used. In any of the embodiments disclosed herein the material may be annealed. In any of the embodiments, the material may be formed or cut into sheets, threads, or three dimensional shapes can be made. In certain embodiments, a dye may be used to achieve a characteristic color or to make the material radio-opaque. In any of the embodiments, a step of applying pressure or compressing the material may be used to condense the material, improve thickness control or for some other reason. Therefore, the above description should not be construed as limited, but merely as exemplifications of particular embodiments. Those skilled in the art will envision other modifications within the scope and spirit of the claims appended hereto.

What is claimed is:

1. A method of making a nonwoven fiber mat, comprising:
providing a material, an extruder and a bimodal spinneret, wherein the spinneret defines first holes each having a first diameter and second holes each having a second diameter different than the first diameter, the first and second holes disposed along a longitudinal axis of the spinneret, at a nadir of a cavity of the spinneret, in a pattern of alternating first and second diameters wherein each of the first holes is disposed axially adjacent to one of the second holes;
coupling the spinneret to the extruder;
feeding the material into the extruder;
melting the material in the extruder;
passing the melted material into the spinneret;
extruding an equal number of first and second fibers through the respective first and second holes of the spinneret in the pattern of alternating first and second diameters; and
collecting the first and second fibers onto a conveyer surface to form a nonwoven fiber mat.

2. The method of claim 1, wherein the material is a polymer selected from the group consisting of lactide homopolymer, glycolide homopolymer, polydioxanone homopolymer, glycolide trimethylene carbonate copolymer, glycolide lactide copolymer, glycolide dioxanone trimethylene carbonate copolymer, and glycolide caprolactone trimethylene carbonate lactide copolymer.

3. The method of claim 1, wherein the material is a bioabsorbable polymeric material.

4. The method of claim 1, wherein the melting temperature of the material is between about 180 and about 270 degrees Celsius.

5. The method of claim 1, wherein the melting temperature of the material is between about 80 degrees Celsius and about 190 degrees Celsius.

6. The method of claim 1, further including blowing hot air on the first and second fibers as they exit the spinneret and before they are collected on the conveyer surface.

7. The method of claim 6, wherein the hot air has a temperature greater than or equal to the melting temperature of the first and second fibers.

8. The method of claim 6, wherein the hot air has a temperature of between about 225 and about 290 degrees Celsius.

9. The method of claim 6, further including plasma treating at least a portion of a surface of the nonwoven fiber mat with an ionizable gas species or combination of ionizable gas species configured to chemically modify or functionalize the surface of the nonwoven fiber mat.

10. The method of claim 9, further including applying heat and pressure to the nonwoven fiber mat before plasma treating the nonwoven fiber mat.

11. The method of claim 9, further including cutting the nonwoven fiber mat.

12. The method of claim 11, wherein cutting the nonwoven mat includes cutting the nonwoven fiber mat into a shape corresponding to the shape of a tissue contacting surface of a surgical stapler.

13. The method of claim 6, further including allowing the first and second fibers to cool on the conveyer surface after blowing hot air on the first and second fibers to form the nonwoven fiber mat.

14. A method of making a nonwoven fabric surgical implant, the method comprising:
- passing melted bioabsorbable material into a spinneret defining first holes each having a first diameter and second holes each having a second diameter different from the first diameter, the first and second holes disposed along a longitudinal axis of the spinneret, at a nadir of a cavity of the spinneret, in a pattern of alternating first and second diameters wherein each of the first holes is disposed axially adjacent to one of the second holes;
- extruding an equal number of first and second fibers through the respective first and second holes of the spinneret in the pattern of alternating first and second diameters;
- depositing the first and second fibers on a conveyor surface; and
- cooling the first and second fibers on the conveyor surface to form a nonwoven fabric surgical implant.

15. The method of claim 14, further including applying heat and pressure to the first and second fibers before cooling the first and second fibers.

16. The method of claim 15, wherein applying heat includes blowing hot air onto the first and second fibers exiting the spinneret to force the first and second fibers onto the conveyor surface.

17. The method of claim 16, wherein applying pressure includes applying suction through the conveyor surface to compact the first and second fibers against each other.

18. The method of claim 15, further comprising:
- transporting the nonwoven fabric surgical implant on the conveyor surface to a plasma apparatus; and
- plasma treating at least a portion of a surface of the nonwoven fabric surgical implant with an ionizable gas species or combination of ionizable gas species configured to chemically modify or functionalize the surface of the nonwoven fabric surgical implant.

19. The method of claim 18, further comprising:
- transporting the nonwoven fabric surgical implant on the conveyor surface from the plasma apparatus to a cutting apparatus; and
- cutting the nonwoven fabric surgical implant.

20. The method of claim 8, wherein extruding an equal number of first and second fibers includes melt extruding the first and second fibers at a temperature between about 140 and about 185 degrees Celsius.

\* \* \* \* \*